United States Patent [19]

Motoi et al.

[11] Patent Number: 4,977,307
[45] Date of Patent: Dec. 11, 1990

[54] APPARATUS FOR HEATING SAMPLE WITHIN VACUUM CHAMBER

[75] Inventors: Yoshihiko Motoi, Kyoto; Naoki Yamamoto, Kawaguchi; Yukio Takano, Musashimurayama, all of Japan

[73] Assignee: Horiba, Ltd., Kyoto, Japan

[21] Appl. No.: 298,558

[22] Filed: Jan. 17, 1989

[30] Foreign Application Priority Data

Jan. 20, 1988 [JP] Japan ................................. 63-11319

[51] Int. Cl.$^5$ ............................................. H05B 1/00
[52] U.S. Cl. .................................. 219/392; 219/390; 219/392; 432/205; 422/78; 422/95
[58] Field of Search ............... 219/385, 391, 392, 210, 219/390, 405, 411, 388; 432/205, 242, 220; 422/78, 95, 99

[56] References Cited

U.S. PATENT DOCUMENTS

| 4,430,055 | 2/1984 | Sugiyama | 432/205 |
| 4,751,372 | 6/1988 | Fraas | 219/553 |
| 4,820,907 | 4/1989 | Terauchi | 219/494 |

OTHER PUBLICATIONS

IBM Technical Bulletin, G. F. Barber, Two Chamber Air to Vacuum Lock System, vol. 11, No. 7, 12/68, 757–758.

Primary Examiner—Bruce A. Reynolds
Assistant Examiner—Leon K. Fuller
Attorney, Agent, or Firm—Price, Gess & Ubell

[57] ABSTRACT

An apparatus for heating a sample within a vacuum chamber according to the present invention includes a preliminary exhaust chamber connected with a vacuum chamber of an analyzer and the like through a gate valve. A sample stage is disposed within the vacuum chamber, and a sample holder is detachably disposed on this stage. The preliminary exhaust chamber is provided with a transfer device for transferring the sample holder between the preliminary exhaust chamber and the vacuum chamber to mount the sample holder on the stage and detach the sample holder from the stage. The sample holder is provided with a heater and a temperature-measuring element mounted thereon, the heater and temperature-measuring element being connected with the respective connectors mounted on the sample holder. A fixed connector is connected with the connectors when the sample holder is mounted on the stage by means of the transfer device.

13 Claims, 4 Drawing Sheets

APPARATUS FOR HEATING SAMPLE WITHIN VACUUM CHAMBER

BACKGROUND OF THE INVENTION

1. Field of the Invention

The present invention generally relates to an apparatus for heating a sample within a vacuum chamber in an analyzer, and others provided with said vacuum chamber, and adapted to heat the sample set within the vacuum chamber.

2. Description of Related Art

As to an analyzer and others, for example, an apparatus shown in FIG. 5 has been known as an apparatus for heating a sample within a vacuum chamber. Reference numeral 51 designates a vacuum chamber provided with a take-in and out opening 53 adapted to be capable of opening and closing by means of a cover 52 for taking the sample in and out. Reference numeral 54 designates a bracket fixedly mounted on an inner surface of the cover 52. A heating block 56 comprising a heater and a temperature-measuring element is mounted on a stage 55 which is mounted on the bracket 54. An upper portion of the heating block 56 serves as a sample table 57. A wiring 58 for the heating block 56 passes through the cover 52 to be taken out of the vacuum chamber 51. Reference numeral 59 designates a packing mounted on a mouth portion of the take-in and out opening 53.

In this apparatus, in the case where the sample is mounted on the sample table 57, the cover 52 is separated from the vacuum chamber 51 to take out everything, including the heating block 56 of the vacuum chamber 51 with the stage 55, and mount the sample on the sample table 57.

Everything, including the heating block 56, is inserted into the vacuum chamber 51 through the cover 52 and the take-in and out opening 53 is closed with the cover 52 to evacuate the vacuum chamber 51.

When the sample is separated from the sample table 57, the whole including the heating block 56 is taken out of the vacuum chamber 51 through the cover 52. When the sample is mounted on and detached from the sample table 57, the vacuum chamber 51 is opened to the air.

Also, a heating apparatus shown in FIG. 6 has been known. Reference numeral 61 designates a bottom plate on which a bell jar 62 is placed. Reference numeral 63 designates a stage mounted on the bottom plate 61. A heating block 64 comprising a heater and a temperature-measuring element is mounted on the stage 63, and an upper portion of the heating block 64 serves as a sample table 65. A wiring 66 of the heating block 64 passes through the bottom plate 61 to be taken out. Reference numeral 67 designates a packing mounted on the bell jar 62.

In this apparatus, the sample is mounted on and detached from the sample table by separating the bell jar 62 from the bottom plate 61 to expose the sample table 65.

PROBLEMS TO BE SOLVED BY THE INVENTION

With the apparatus shown in FIG. 5, the whole including the heating block 56 is taken out of the vacuum chamber 51 together with the stage 55 through the cover 52 every time for mounting and detaching the sample, so that a problem occurs in that it requires much labor. In addition, the vacuum chamber 51 is opened to the air every time for mounting and detaching the sample, so that a problem occurs also in that in order to evacuate the vacuum chamber 51 again, it requires much labor.

With the apparatus shown in FIG. 6, it is necessary to move the bell jar 62 every time for mounting and detaching the sample, so that it requires much labor. In addition, the bell jar 62 is opened to the air every time for mounting and detaching the sample, so that a problem occurs in that it is necessary to evacuate the bell jar 62 every time for mounting and detaching the sample.

With both apparatuses, in the case where the sample is heated within the vacuum chamber, the heater is used, so that the wiring for the heater is required. Accordingly, it is impossible to make the heating block mountable on and detachable from the stage to transfer the heating block from the preliminary exhaust chamber to the vacuum chamber because of the wiring, whereby problems have occurred.

SUMMARY OF THE INVENTION

The present invention solves the above-described problems and it is an object of the present invention to provide an apparatus for heating a sample within a vacuum chamber in which it is unnecessary to open the vacuum chamber to the air for mounting and detaching the sample by providing a preliminary exhaust chamber in the vacuum chamber.

MEASURES FOR SOLVING THE PROBLEMS

An apparatus for heating a sample within a vacuum chamber according to the present invention is characterized by a preliminary exhaust chamber connected with a vacuum chamber of an analyzer and the like through a gate valve. A sample stage is disposed within the vacuum chamber, and a sample holder is detachably disposed on this stage. The preliminary exhaust chamber is provided with a transfer device for transferring the sample holder between the preliminary exhaust chamber and the vacuum chamber to mount the sample holder on the stage and detach the sample holder from the stage. The sample holder is provided with a heater and a temperature-measuring element mounted thereon, the heater and temperature-measuring element being connected with the respective connectors mounted on the sample holder. A fixed connector is connected with the connectors when the sample holder is mounted on the stage by means of the transfer device.

OPERATION

According to this apparatus for heating the sample within the vacuum chamber, the gate valve is closed and then the sample holder, on which the sample has been mounted, is mounted on the transfer device in the preliminary exhaust chamber. The preliminary exhaust chamber is evacuated under this condition and then the gate valve is opened to transfer the sample holder to the vacuum chamber by means of the transfer device and mounted on the stage.

Upon mounting the sample holder on the stage in the above-described manner, the respective connectors connected with the heater and temperature-measuring element provided in the sample holder are connected with the fixed connectors disposed within the vacuum chamber to apply a voltage to the heater and temperaturemeasuring element.

BRIEF DESCRIPTION OF THE DRAWINGS

One preferred embodiment of the present invention is show in FIGS. 1 to 4, in which.

DETAILED DESCRIPTION OF THE PREFERRED EMBODIMENTS

Figure 1:
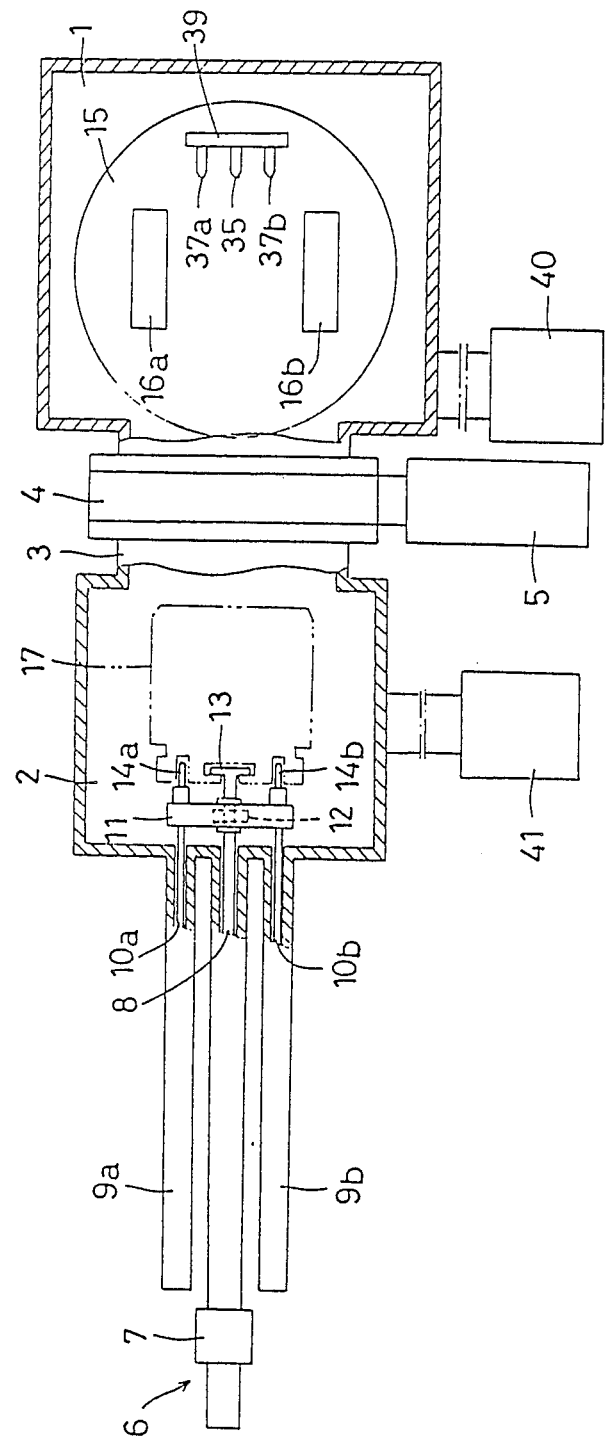
FIG. 1 is a sectional view.

One preferred embodiment of the apparatus for heating a sample within a vacuum chamber according to the present invention is described with reference to FIGS. 1 to 4.

Referring to FIGS. 1 to 4, reference numeral 1 designates a vacuum chamber. Reference numeral 2 designates a preliminary exhaust chamber opening into the vacuum chamber 1, the preliminary exhaust chamber 2 being able to be opened into the vacuum chamber 1. The vacuum chamber 1 is able to be closed by providing a gate valve 4 in a communicating portion 2 between the vacuum chamber 1 and the preliminary exhaust chamber 2. The gate valve 4 is operated by means of a cylinder 5, thereby opening and closing the communicating portion 3.

Reference numeral 6 designates a magnetic coupling-type transfer device disposed in the preliminary exhaust chamber 2 and is adapted to transfer an operating shaft 8 from inside the preliminary exhaust chamber 2 to inside the vacuum chamber 1 or oppositely to the above-described by sliding a dial 7 of the transfer device 6 and rotate the operating shaft 8 by rotating the dial 7.

Reference numerals 9a, 9b designate cylindrical rectilinear propagation guides disposed within the preliminary exhaust chamber 2 and arranged on both sides of the transfer device 6 nearly in parallel to the transfer device 6. The guides are provided with guide rods 10a, 10b slidably inserted therein, respectively. Reference numeral 11 designates a holding member mounted on each pointed end of the guide rods 10a, 10b. The pointed end portion of the operating shaft 8 is rotatably and unslidably mounted on the holding member 11 while passing through the holding member 11. Reference numeral 12 designates a bearing for holding the operating shaft 8.

Upon sliding the operating shaft 8 by operating the dial 7, the guide rods 10a, 10b are simultaneously slid through the holding member 11, whereby the holding member 11 goes straight on without rotating.

Reference numeral 13 designates a rod-like hook fixedly mounted on a pointed end of the operating shaft 8 so as to meet at right angles with the operating shaft 8. Reference numerals 14a, 14b designate holding pins projecting from the holding member 11 on both sides of the operating shaft 8. These holding pins 14a, 14b are almost coaxial with the guide rods 10a, 10b, but they may be disposed at positions different from those of the guide rods 10a, 10b.

Reference numeral 15 designates a stage disposed within the vacuum chamber 1 for mounting a sample holder, which will be described later, and which is transferred by means of the transfer device 6. The stage is also provided with a pair of fitting members 16a, 16b having a reverse L-shaped section fixedly mounted on a surface thereof at an interval, parallel to each other, and with gap portions thereof opposite to each other (refer to FIG. 4).

Reference numeral 17 designates a sample holder (refer to FIG. 2) provided with an opening 19 into which the hook 13 can be inserted in the direction of thickness thereof. The opening is formed in an end face of a support member 18 at one end thereof, and an engaging hole 20 into which the hook 13 can be inserted in the direction of length thereof is formed so as to be opened into the opening 19. The hook 13 is inserted into the engaging hole 20 from the opening 19 in the direction of thickness thereof and then the operating shaft 8 is rotated by about 90 degrees to engage the hook 13 with the engaging hole 20.

Reference numerals 21a, 21b designate inserting holes formed in end faces of the sample holder 17 on both sides of the opening 19, the distances from these inserting holes 21a, 21b to the opening 19 being equal to distances from the hook 13 to the holding pins 14a, 14b so that the holding pins 14a, 14b can be inserted into the inserting holes 21a, 21b.

Reference numerals 22a, 22b designate engaging plates disposed on both sides of the sample holder 17 and adapted to mount the sample holder 17 on the stage 15 by engagedly inserting them between the fitting members 16a, 16b.

Reference numeral 23 designates an insulator provided with a sample table 24 buried in a central portion, a heater 25 on a circumferential surface thereof, and a temperature-measuring element 26, such as a thermocouple or platinum resistance-measuring element, on a reverse side thereof. The insulator 23 is mounted on end portions of a plurality of support plates 28 which are mounted on a frame-like fitting table 27 at one end thereof fixedly mounted on an upper surface of the sample holder 17 and projected inward. The insulator 23 is arranged inside the fitting table 27 in a hanging manner.

Reference numerals 29a, 29b designate connectors with which the heater 25 is connected. Reference numerals 30a, 30b designate connectors with which the temperature-measuring element 26 is connected. Reference numerals 30c, 30d designate supplementary connectors disposed opposite to the connectors 30a, 30b. These connectors 29a, 29b, 30a, 30b, 30c, 30d are fixedly mounted on the fitting member 27 at an end portion opposite to the support member 18 of the sample holder 17.

Reference numeral 31 designates a sample-fixing member disposed in the sample table 24. Reference numeral 32 designates a sample. Reference numeral 33 designates ring heat-reflecting plates disposed below and on side portions of the insulator 23 for reflecting radiant heat from the circumferential surface and reverse surface of the insulator 23 to improve heating efficiency. Reference numeral 34 designates support rods for the heat-reflecting plate 33.

Reference numeral 35 designates fixed connectors inserted between the connectors 29a, 29b and are provided with terminals 36a, 36b on a surface brought into contact with the connectors 29a, 29b, respectively. Reference numerals 37a, 37b designate fixed connectors inserted between the connector 30a and the supplementary connector 30c and between the connector 30b and the supplementary connector 30d and are provided with terminals 38a, 38b brought into contact with the connectors 30a, 30b.

The fixed connectors 35, 37a, 37b project from a side surface of a fitting plate 39 standing on a surface of the stage 15 and adapted to be inserted between the connector 29a and the connector 29b, the connector 30a and the supplementary connector 30c, and the connector 30b and the supplementary connector 30d, respectively, when they are engaged with the fitting members 16a, 16b to mount the sample holder 17 on the stage 15.

The respective lead wires (not shown) connected with the terminals 36a, 36b, 38a, 38b, respectively, are taken out of the vacuum chamber 1.

Reference numeral 40 designates a vacuum pump connected with the vacuum chamber 1. Reference numeral 41 designates a vacuum pump connected with the preliminary exhaust chamber 2.

The preliminary exhaust chamber 2 is provided with a mouth (not shown) which is capable of being opened and closed by means of a cover for taking the sample holder 17 in and out therefrom.

In this apparatus, the sample 32 is fixedly mounted on the sample table 24 of the sample holder 17 by means of the sample-fixing member 31. In the case where this sample holder 17 is mounted on the stage 15 of the vacuum chamber 1, the cylinder 5 is operated to close the gate valve 4. The sample holder 17 is put in the preliminary exhaust chamber 2 and the dial 7 is operated to rotate the operating shaft 8, whereby the hook 13 of the operating shaft 8 is inserted into the engaging hole 20 through the mouth 19, and the holding pins 14a, 14b are inserted into the inserting holes 21a, 21b of the sample holder 17.

Figure 2:
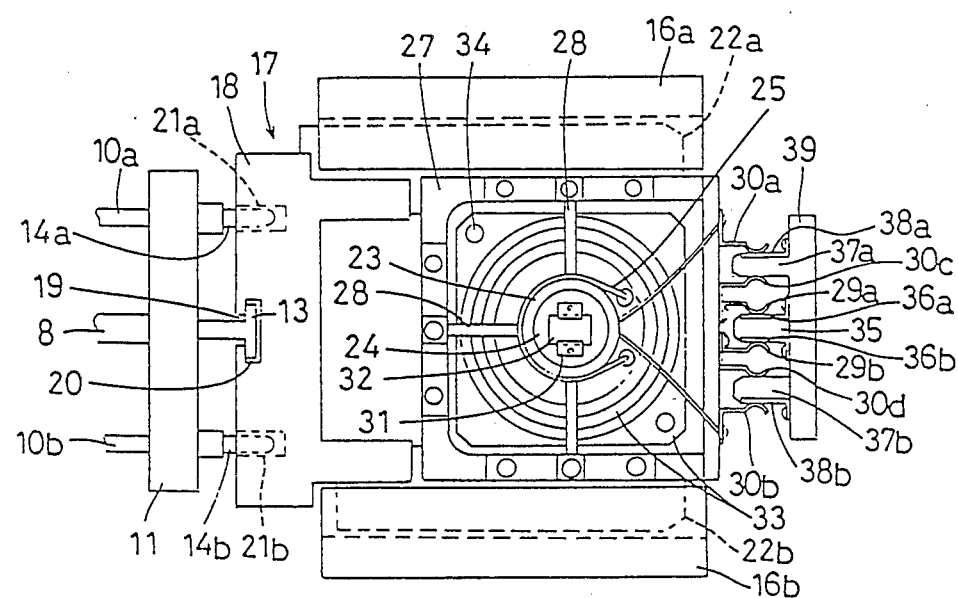
FIG. 2 is an enlarged plan view showing a sample holder and a stage.
Figure 3:
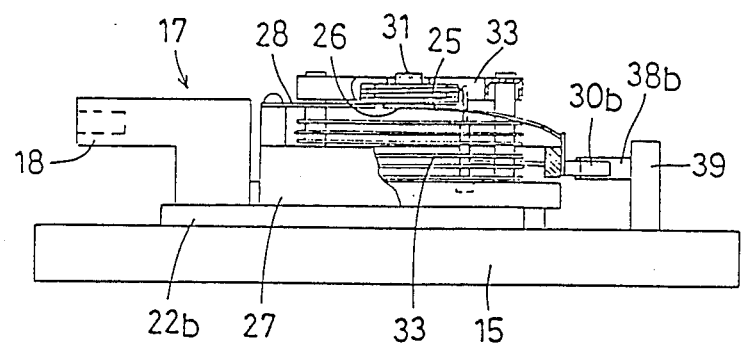
FIG. 3 is an front view showing the sample holder and the stage.
Figure 4:
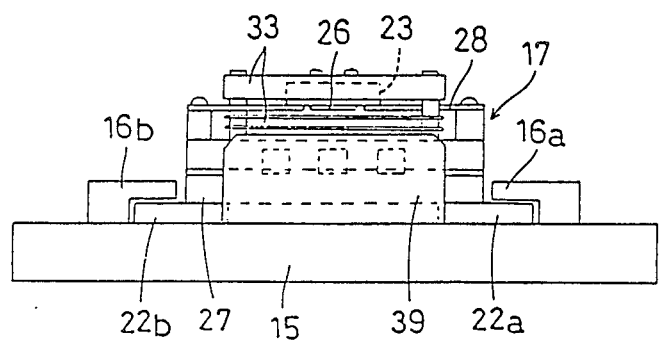
FIG. 4 is a side view showing the sample holder and the stage.
Figure 5:
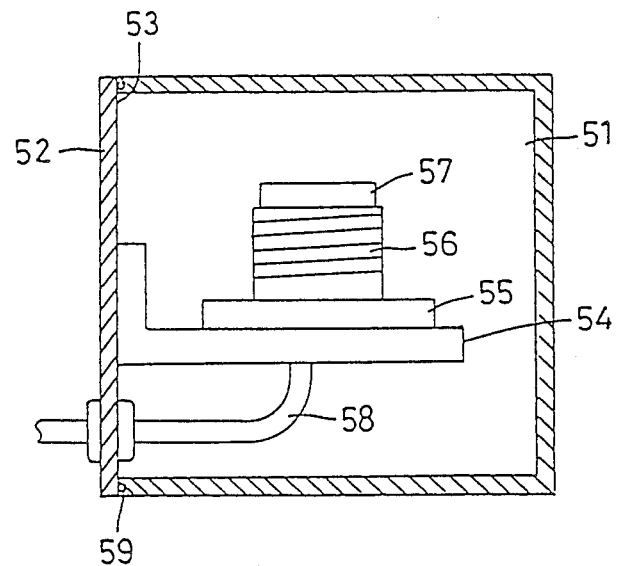
FIGS. 5, 6 are sectional views showing the conventional examples different from each other.
Figure 6:
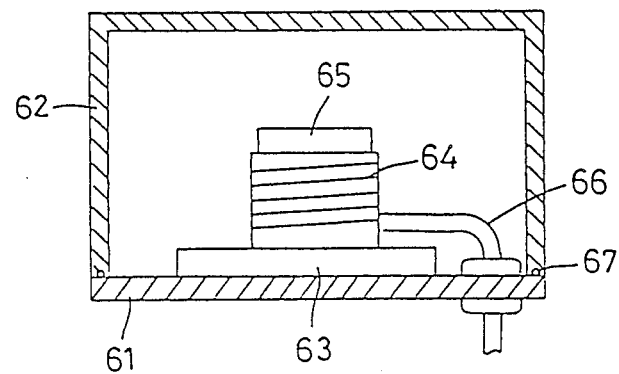

Subsequently, the hook 13 is rotated by almost 90 degrees, by means of the operating shaft 8, to be engaged with the engaging hole 20 and mount the sample holder 17 on the transfer device 6 (refer to FIGS. 1, 2). Under this condition, the preliminary exhaust chamber 2 is closed tightly to be evacuated by driving the vacuum pump 41.

Upon evacuating the preliminary exhaust chamber 2, the gate valve 4 is opened and the dial 7 is slid to insert the operating shaft 8 into the vacuum chamber 1 together with the guide rods 10a, 10b, and transfer the sample holder 17 along the surface of the stage 15, whereby the engaging plates 22a, 22b are engagedly inserted into the gap between the fitting members 16a, 16b to mount the sample holder 17 on the stage 15.

Thereupon, the fixed connector 35 is inserted between the connectors 29a and 29b and the fixed connectors 35b, 37a, 37b are inserted between the connectors 30a, 30b and the supplementary connectors 30c, 30d, respectively, to connect the connectors 29a, 29b, 30a, 30b with the terminals 36a, 36b, 38a, 38b.

Upon mounting the sample holder 17 on the stage 15, the operating shaft 8 is rotated by operation of the dial 7. The hook 13 is set so as to be parallel to the opening 19, and then the operating shaft 8 is retreated to separate the hook 13 and the holding pins 14a, 14b from the sample holder 17.

A sample 32 mounted on the sample table 24 of the sample holder 17 is heated by applying a voltage to the heater 25 through the terminals 36a, 36b and the connectors 29a, 29b and heating the sample table 24 mounted on the insulator 23 in a burried manner. The temperature control is carried out on the basis of a signal put out from the temperature-measuring element 26 mounted on the rear surface of the insulator 23 through the connectors 30a, 30b and the terminals 38a, 38b.

As above described, the sample holder 17, on which the sample 32 is mounted, is mounted on the stage 15 disposed within the vacuum chamber 1 to heat the sample 32, so that the preliminary exhaust chamber 2 can be connected with the vacuum chamber 1 to mount the sample holder 17 on the stage 15 within the vacuum chamber 1 through the preliminary exhaust chamber 2, as in this preferred embodiment.

Accordingly, it is not required to open the vacuum chamber 1 to the air by opening and closing the gate valve 4 when the sample is mounted and detached, whereby the sample 32 can be easily and efficiently mounted and detached.

The sample holder 17 is mounted on the transfer device 6 within the preliminary exhaust chamber 2 to evacuate the inside of the preliminary exhaust chamber 2, and then the sample holder 17 is transferred into the vacuum chamber 1 so that water and the like adhered to the sample holder 17 can be preliminarily removed in the preliminary exhaust chamber 2. Thus, gases can be prevented from being generated within the vacuum chamber 1 so as to easily achieve the object of heating the sample in a vacuum.

The heater 25 is mounted on the circumferential surface of the insulator 23 and the sample table 24 is mounted on the insulator 23 in a burried manner, so that the sample table 24 can be efficiently heated to efficiently heat the sample at the desired temperature.

This apparatus, as above described, can mount the sample holder 17 provided with the heater 25 and the temperature-measuring element 26 on the stage 15 within the vacuum chamber 1 through the preliminary exhaust chamber 2 or separate the sample holder 17 from the stage 15 to, for example, heat and analyze the sample. It can also be used in the case where the analysis and the like of the sample are carried out without heating the sample. Also, the sample holder, which is used in that case, provided with no heater 25 and temperature-measuring element 26, can be mounted on the stage 15 by means of the transfer device 6 in the above-described manner.

In addition, the connectors 29a, 29b, 30a, 30b and the fixed connectors 35, 37a, 37b having an optional construction, which can be connected and separated by moving along a surface of the stage 15, can be used to mount the sample holder 17 onto the stage 15. Also, the O-ring seal-type transfer device 6 can be used. A screw shaft can be used in place of the hook 13 of the operating shaft 8. In this case, the sample holder 17 is provided with a threaded hole.

Effects of the Invention

According to the apparatus for heating a sample within a vacuum chamber of the present invention, as above described, the sample holder, which is detachably mounted on the stage disposed within the vacuum chamber, is provided with the heater and the temperature-measuring element, the heater and the temperature-measuring element being connected with the connectors mounted on the sample holder, and the respective connectors being connected with the respective fixed connectors disposed within the vacuum chamber, whereby the sample holder can be taken in and out of the vacuum chamber through the preliminary exhaust chamber connected with the vacuum chamber.

Accordingly, it is not required to open the vacuum chamber to the air when the sample is mounted and detached, so that the sample holder can be easily and efficiently mounted on and detached from the vacuum chamber. The sample holder is mounted on the transfer device within the preliminary exhaust chamber and the preliminary exhaust chamber is evacuated, and then the sample holder is transferred into the vacuum chamber, so that water and the like adhered to the sample holder can be removed in the preliminary exhaust chamber to maintain the vacuousness within the vacuum chamber, thereby more surely achieving the object of heating the sample in a vacuum.

In addition, the connection and separation of the connectors mounted on the sample holder with and from the fixed connectors disposed within the vacuum chamber are carried out by the movement of the sample holder for mounting the sample holder on and detaching it from the stage, so that the special labor for connecting the connectors with the fixed connectors and separating the connectors from the fixed connectors is not required, whereby efficiently and surely connecting and separating is achieved.

What is claimed is:

1. An apparatus for heating a sample within a vacuum chamber, comprising:
   a preliminary exhaust chamber connected with said vacuum chamber through a gate valve;
   a sample stage disposed within said vacuum chamber;
   a sample holder detachably disposed on said stage;
   said preliminary exhaust chamber being provided with a transfer device for transferring said sample holder between said preliminary exhaust chamber and said vacuum chamber to mount said sample holder on said stage and detach said sample holder from said stage;
   said sample holder being provided with a heater and a temperature-measuring element mounted thereon, said heater and temperaturemeasuring element being connected with respective connectors mounted on said sample holder; and
   a fixed connector, which is connected with said connectors when said sample holder is mounted on the stage by means of said transfer device, being disposed within said vacuum chamber.

2. The apparatus according to claim 1 further comprising first vacuum means for vacuuming said preliminary exhaust chamber and second vacuum means for vacuuming said vacuum chamber.

3. The apparatus according to claim 1 further comprising guide means for guiding said sample holder in a linear direction.

4. The apparatus according to claim 1 further comprising holding means for holding said sample holder to said transfer device.

5. An apparatus for heating a sample within a vacuum chamber of an analyzer, comprising:
   a preliminary exhaust chamber which can be in opened and closed communication with said vacuum chamber, said exhaust chamber capable of being evacuated separately from said vacuum chamber;
   a sample holding means for holding a sample in said exhaust chamber;
   a transfer means for transferring said sample holding means between said exhaust chamber and said vacuum chamber; and
   receiving means for receiving and releasing said sample holding means, said receiving means being disposed in said vacuum chamber.

6. The apparatus according to claim 5 further comprising gate means for regulating said opened and closed communication.

7. The apparatus according to claim 5 further comprising heating means for heating said sample, said heating means being mounted on said sample holding means.

8. The apparatus according to claim 7 further comprising electrical connection means for electrically connecting said heating means to a power source as said sample holding means is received by said receiving means.

9. The apparatus according to claim 7 further comprising a sample table means for holding said sample and which can be heated by said heating means to thereby heat said sample.

10. A method of heating a sample in a vacuum chamber for subsequent analysis, comprising the steps of:
    placing said sample on a sample holder;
    evacuating a first chamber in which said sample holder is placed;
    opening said first chamber to a second chamber;
    transferring said sample holder from said first chamber to said second chamber in the absence of exposure to air; and
    connecting said sample holder to a power source upon said sample holder being transferred into said second chamber such that said sample holder may heat said sample.

11. The method of heating according to claim 10 further comprising the step of mounting said sample holder on a stage disposed in said second chamber.

12. The method of heating according to claim 10 further including the step of regulating an opening and closing of said first chamber.

13. The method of heating according to claim 10 further including the step of providing a transfer means for engaging and disengaging said sample holder and transferring said sample holder between said first and second chambers.

* * * * *